(12) United States Patent
Don et al.

(10) Patent No.: US 7,141,022 B1
(45) Date of Patent: Nov. 28, 2006

(54) METHOD FOR ALIGNING DERIVED-BAND ABR RESPONSES BASED ON INTEGRATION OF DETRENDED DERIVED-BAND ABRS

(75) Inventors: Manuel Don, Anaheim, CA (US); Curtis W. Ponton, El Paso, TX (US)

(73) Assignee: House Ear Institute, Los Angeles, CA (US)

( * ) Notice: Subject to any disclaimer, the term of this patent is extended or adjusted under 35 U.S.C. 154(b) by 205 days.

(21) Appl. No.: 10/818,806

(22) Filed: Apr. 5, 2004

Related U.S. Application Data

(60) Provisional application No. 60/460,494, filed on Apr. 3, 2003.

(51) Int. Cl.
*A61B 5/00* (2006.01)
(52) U.S. Cl. ..................................... 600/559
(58) Field of Classification Search ............... 600/300, 600/303, 373, 377–379, 544–545, 559
See application file for complete search history.

(56) References Cited

U.S. PATENT DOCUMENTS

| | | | | |
|---|---|---|---|---|
| 4,493,327 A * | 1/1985 | Bergelson et al. | .......... | 600/544 |
| 5,003,986 A * | 4/1991 | Finitzo et al. | .............. | 600/544 |
| 5,230,344 A * | 7/1993 | Ozdamar et al. | ............ | 600/544 |
| 5,392,788 A * | 2/1995 | Hudspeth | ...................... | 600/544 |
| 6,001,065 A * | 12/1999 | DeVito | ......................... | 600/544 |
| 6,024,700 A * | 2/2000 | Nemirovski et al. | ......... | 600/300 |
| 6,080,112 A | 6/2000 | Don | | |
| 6,120,441 A * | 9/2000 | Griebel | ....................... | 600/300 |
| 6,264,616 B1 | 7/2001 | Don | | |
| 6,358,201 B1* | 3/2002 | Childre et al. | .............. | 600/300 |
| 6,385,486 B1* | 5/2002 | John et al. | .................... | 600/544 |
| 6,475,163 B1* | 11/2002 | Smits et al. | ................. | 600/559 |
| 6,687,525 B1* | 2/2004 | Llinas et al. | ................. | 600/407 |
| 6,968,228 B1* | 11/2005 | Thornton | ..................... | 600/544 |
| 2002/0091335 A1* | 7/2002 | John et al. | .................... | 600/544 |
| 2003/0073920 A1* | 4/2003 | Smits et al. | ................. | 600/544 |
| 2003/0144603 A1* | 7/2003 | Zoth et al. | .................... | 600/559 |

\* cited by examiner

*Primary Examiner*—Max Hindenburg
*Assistant Examiner*—Rene Towa
(74) *Attorney, Agent, or Firm*—Blakely, Sokoloff, Taylor & Zafman LLP

(57) ABSTRACT

In a diagnostic system wherein a patient's auditory brainstem response (ABR) to each of a plurality of auditory stimuli is recorded and wherein a plurality of derived-band ABRs representing cochlear responses in a plurality of respective frequency bands are constructed, the derived-band ABRs are temporarily aligned based on observable peaks in integrated, detrended derived-band waveforms.

8 Claims, 2 Drawing Sheets

METHOD FOR ALIGNING DERIVED-BAND ABR RESPONSES BASED ON INTEGRATION OF DETRENDED DERIVED-BAND ABRS

RELATED APPLICATION

This application claims the benefit of provisional application Ser. No. 60/460,494 filed on Apr. 3, 2003.

BACKGROUND OF THE INVENTION

1. Field of the Invention

This invention relates generally to the field of otological diagnostic procedures. More particularly, the invention relates to a method for aligning derived-band auditory brainstem responses (ABRs) to acoustic stimuli.

2. Background

U.S. Pat. Nos. 6,080,112 and 6,264,616, the disclosures of which are incorporated herein by reference, disclose a diagnostic technique for detecting small ($\leq 1$ cm) intracanalicular tumors. The procedure first records a patient's auditory brainstem response (ABR) to each of a plurality of auditory stimuli. The stimuli comprise 60 dB nHL clicks using high pass noise masking procedures to isolate the cochlear response within specific frequency bands. These derived band ABRs are temporally shifted to align the wave V peak amplitudes. The time-shifted responses are then summed to create a "stacked ABR". The stacked wave V ABR amplitude is compared to a threshold value. The stacked wave V ABR amplitudes for patients having small (less than or equal to 1 cm.) intracanalicular tumors are measurably lower than those for otherwise similar individuals without tumors.

In the above-referenced patents, the derived-band response waveforms are aligned according to the peak latencies of wave V in each derived-band response. However, the alignment process depends on operator judgment and it is often difficult to determine where the peak of wave V occurs for some of the derived-band responses. This invention provides a different way of aligning the responses before the summation process and avoids having the operator make decisions about where the peak latency of wave V occurs for the derived bands.

SUMMARY OF THE INVENTION

The present invention provides a method of temporally aligning derived-band ABRs comprising: fitting each of the derived-band ABRs to a respective linear equation; subtracting the linear equation from the respective derived-band ABR to obtain a detrended derived-band ABR; calculating an integral function for each of the detrended derived-band ABRs; identifying a peak in each of the integral functions; calculating a respective peak displacement value for each of the integral functions; and shifting each of the detrended derived-band ABRs by the respective displacement value.

DETAILED DESCRIPTION OF THE INVENTION

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Figure 1:
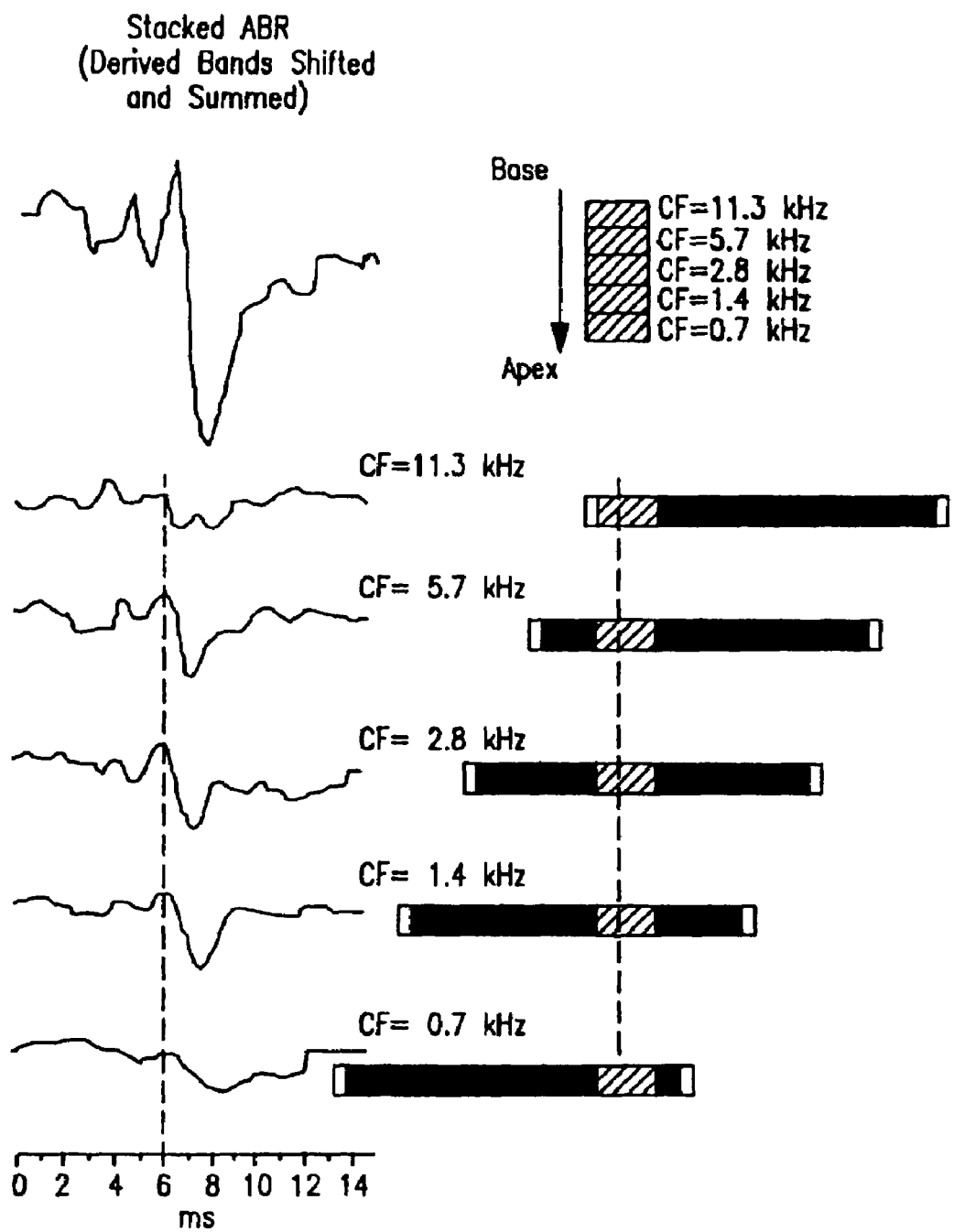
FIG. 1 illustrates the temporal shifting of derived-band ABRs to create a stacked ABR.

FIG. 1 illustrates the construction of a stacked ABR from a plurality of derived-band ABRs corresponding to specific audio frequencies. Each of the derived-band ABRs represents the patent's response to cochlear activity within a band of approximately one octave. As disclosed in U.S. Pat. Nos. 6,080,112 and 6,264,616, a stacked ABR may be constructed by first time shifting the individual derived-band waveforms so that the peak latency of wave V in each waveform coincides and then summing the shifted derived-band waveforms. If the wave V peak of a waveform is not discernable, it is not time shifted, which may introduce errors in the stacked ABR. Furthermore, misidentification of the wave V peak may also introduce errors.

In accordance with the present invention, the derived-band ABR waveforms are aligned based on the voltage zero-crossing of wave V in each derived band. To do this, we first detrend each of the waveforms. This gets rid of any baseline (DC) shift and any linear trend in the data that can affect the latency determination of the true zero-crossing of the derived-band waveform. Next, we perform a simple rectangular integration of the detrended derived-band waveform. This results in an integrated waveform in which the peaks reflect the zero crossings. The largest peak in this integrated waveform will usually be related to wave V of the derived-band response. These integrated waveforms are very smooth (integration essentially removes noise) and the largest peaks are easily defined. A simple peak-picking algorithm can then be used to determine the latencies of these peaks. These peak latencies in the integrated waveforms correspond to wave V zero crossings in the detrended derived bands and are used to shift and align the detrended derived bands to form the Stacked ABR. This is similar to the formation of the Stacked ABR based on alignment of the wave V peaks in the simple derived bands described in the above-referenced patents. However, with the present invention, the derived-band ABR response waveforms are detrended and aligned according to their wave V voltage zero-crossing latencies instead of their wave V peak latencies.

Specifically, the process is as follows:

(1) For each derived band, perform a linear curve fit as shown in FIG. 1. The linear fit is define by: $y = K0 + K1*x$, where y is the derived-band amplitude and x is time.

Figure 2:
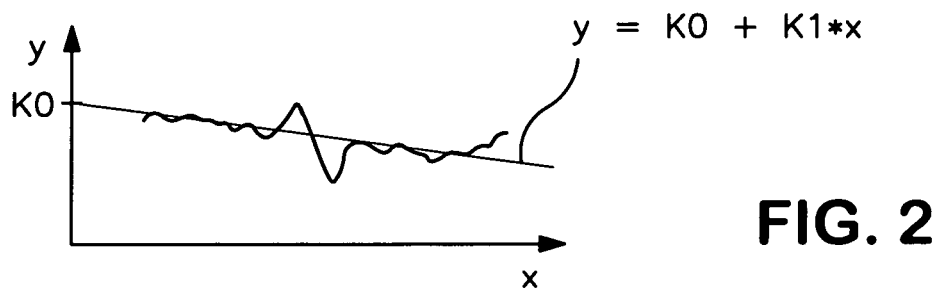
FIG. 2 illustrates linear curve fitting to a derived-band ABR.

(2) Subtract this fitted line from the derived band (derived band−fitted line) as shown in FIG. 2. This will remove any linear trend in the data as well as baseline-correct the data.

(3) Next make a copy of the detrended derived bands.

Figure 3:
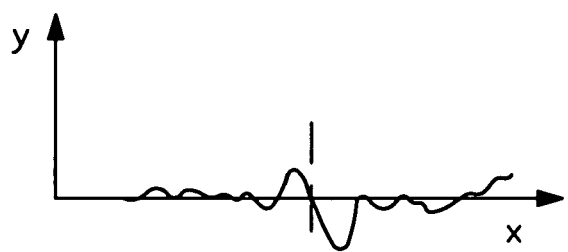
FIG. 3 illustrates detrending of the derived-band ABR of FIG. 2.
Figure 4:
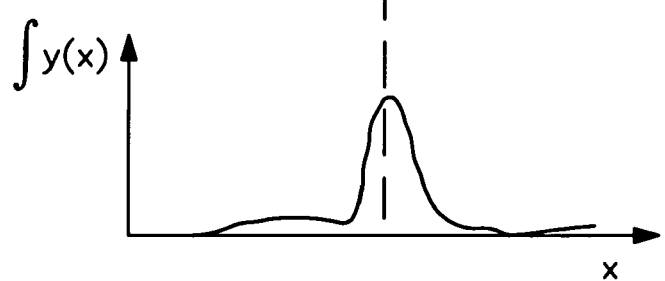
FIG. 4 illustrates an integral function of the detrended derived-band ABR of FIG. 3.

(4) Perform a rectangular integration on each copy of the detrended derived band waveforms as shown in FIG. 3. This integration operation replaces each copy of the detrended derived band with its integral. The X scaling of each wave is taken into account. The computation equation for rectangular integration is:

$$Integderivedband[p] = \sum_{i=0}^{p} derivedband[i] \cdot \Delta x$$

(5) Use any simple peak-picking algorithm to find the latency of the peak (maximum excursion) in the integrated waveform. The latency of the largest peak will usually be related to the zero-crossing of wave V.

(6) Use these peak latencies to align the original detrended derived band waveforms to form the stacked ABR.

In comparison to alignment of the derived-band waveforms based on observed wave V peaks, determining the peaks in the integrated waveform is much simpler and less ambiguous. Taking the guesswork out of the peak picking process not only decreases operator error, but increases the efficiency of the test in clinical situations. In addition, aligning to the voltage zero-crossings optimizes both the peak and trough alignment of the derived-band waveforms. Because the measure for tumor detection is the amplitude of the stacked ABR, a peak-to-trough measure of the sum of the aligned derived-band waveforms, optimizing the peak and trough alignment is clearly advantageous.

The present invention may be implemented as a set of instructions stored in a computer-readable storage medium for causing a general purpose computer to perform the above-described method.

It will be recognized that the above-described invention may be embodied in other specific forms without departing from the spirit or essential characteristics of the disclosure. Thus, it is understood that the invention is not to be limited by the foregoing illustrative details, but rather is to be defined by the appended claims.

What is claimed is:

1. A diagnostic method for detecting a hearing anomaly wherein a patient's auditory brainstem response (ABR) to each of a plurality of auditory stimuli is recorded and wherein a plurality of derived-band ABRs representing cochlear responses in a plurality of respective frequency bands are constructed, the method comprising:
    (a) temporally aligning the derived-band ABRs by:
        (i) fitting each of the derived-band ABRs to a respective linear equation;
        (ii) subtracting the linear equation from the respective derived-band ABR to obtain a detrended derived-band ABR;
        (iii) calculating an integral function for each of the detrended derived-band ABRs;
        (iv) identifying a peak in each of the integral functions;
        (v) calculating a respective peak displacement value for each of the integral functions;
        (vi) shifting each of the detrended derived-band ABRs by the respective displacement value;
    (b) summing the shifted detrended derived-band ABRs and comparing the sum to a threshold value to detect a hearing anomaly.

2. The method of claim 1 wherein the respective linear equation is of the form:

$$y=K0+K1*x$$

3. The method of claim 2 wherein the integral function comprises a rectangular integration.

4. The method of claim 1 wherein the integral function is of the form:

$$Integderivedband[p] = \sum_{i=0}^{p} derivedband[i] \cdot \Delta x.$$

5. A computer-readable storage medium containing a set of instructions for causing a general purpose computer to diagnose presence of a hearing anomaly, the set of instructions comprising:
    instructions for fitting each of a plurality of derived-band auditory brain stem responses (ABRs) to a respective linear equation;
    instructions for subtracting the linear equation from the respective derived-band ABR to obtain a detrended derived-band ABR;
    instructions for calculating an integral function for each of the detrended derived-band ABRs;
    instructions for identifying a peak in each of the integral functions;
    instructions for calculating a respective peak displacement value for each of the integral functions;
    instructions for shifting each of the detrended derived-band ABRs by the respective displacement value;
    instructions for summing the shifted detrended derived-band ABRs and comparing the sum to a threshold value;
    instructions for indicating a positive diagnosis of a hearing anomaly if the sum of the shifted detrended derived-band ABRs is below the threshold value.

6. The computer-readable storage medium of claim 5 wherein the respective linear equation is of the form:

$$y=K0+K1*x$$

7. The computer-readable storage medium of claim 5 wherein the integral function comprises a rectangular integration.

8. The computer-readable storage medium of claim 5 wherein the integral function is of the form:

$$Integderivedband[p] = \sum_{i=0}^{p} derivedband[i] \cdot \Delta x.$$

* * * * *